US011540740B2

(12) United States Patent
Nencka et al.

(10) Patent No.: US 11,540,740 B2
(45) Date of Patent: Jan. 3, 2023

(54) SYSTEM AND METHOD FOR FABRICATING ELECTROMAGNETIC FIELD ENHANCING OBJECTS FOR MAGNETIC RESONANCE IMAGING

(71) Applicant: THE MEDICAL COLLEGE OF WISCONSIN, INC., Milwaukee, WI (US)

(72) Inventors: Andrew S. Nencka, Greendale, WI (US); Andrzej Jesmanowicz, Brookfield, WI (US); James S. Hyde, Dousman, WI (US); Eric S. Paulson, Jackson, WI (US); Lutfi Tugan Muftuler, Menomonee Falls, WI (US); Daniel Shefchik, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 368 days.

(21) Appl. No.: 15/312,844

(22) PCT Filed: May 20, 2015

(86) PCT No.: PCT/US2015/031697
§ 371 (c)(1),
(2) Date: Nov. 21, 2016

(87) PCT Pub. No.: WO2015/179475
PCT Pub. Date: Nov. 26, 2015

(65) Prior Publication Data
US 2017/0185072 A1    Jun. 29, 2017

Related U.S. Application Data
(60) Provisional application No. 62/000,692, filed on May 20, 2014.

(51) Int. Cl.
*B33Y 50/00* (2015.01)
*G01R 33/387* (2006.01)
(Continued)

(52) U.S. Cl.
CPC .............. *A61B 5/055* (2013.01); *B33Y 10/00* (2014.12); *B33Y 50/00* (2014.12); *B33Y 50/02* (2014.12);
(Continued)

(58) Field of Classification Search
None
See application file for complete search history.

(56) References Cited

U.S. PATENT DOCUMENTS 6,294,972 B1    9/2001 Jesmanowicz et al.
7,153,135 B1   12/2006 Thomas
(Continued)

OTHER PUBLICATIONS

The International Search Report and Written Opinion dated Oct. 1, 2015 for International Application No. PCT/US2015/031697.

*Primary Examiner* — Qing Yuan Wu
(74) *Attorney, Agent, or Firm* — Quarles & Brady LLP (57) ABSTRACT

Systems and methods for designing and fabricating three-dimensional objects with precisely computed material compositions for use in enhancing electromagnetic fields for magnetic resonance imaging ("MRI") are provided. As examples, the fabricated object can be designed to reduce magnetic field inhomogeneities in the main magnetic field of an MRI system, or to reduce inhomogeneities in a transmit radio frequency ("RF") field (i.e., a $B_1$ field). As examples, the object can be a shim; a housing or other part of an RF coil; a medical device, such as a surgical implant; or component used in a medical device, such as a housing for an implantable medical device.

18 Claims, 3 Drawing Sheets

(51) Int. Cl.

| | |
|---|---|
| *G01R 33/565* | (2006.01) |
| *B29C 64/386* | (2017.01) |
| *B33Y 50/02* | (2015.01) |
| *B33Y 10/00* | (2015.01) |
| *G05B 19/4099* | (2006.01) |
| *A61B 5/055* | (2006.01) |
| *G01R 33/24* | (2006.01) |
| *A61B 5/05* | (2006.01) |

(52) U.S. Cl.
CPC ....... *G01R 33/387* (2013.01); *G01R 33/5659* (2013.01); *G05B 19/4099* (2013.01); *A61B 5/05* (2013.01); *G01R 33/243* (2013.01); *G01R 33/246* (2013.01)

(56) References Cited

U.S. PATENT DOCUMENTS

| | | |
|---|---|---|
| 2006/0208732 A1 | 9/2006 | Shen et al. |
| 2011/0156704 A1 | 6/2011 | Boernert et al. |
| 2013/0337277 A1 | 12/2013 | Dikovsky et al. |

SYSTEM AND METHOD FOR FABRICATING ELECTROMAGNETIC FIELD ENHANCING OBJECTS FOR MAGNETIC RESONANCE IMAGING

CROSS-REFERENCE TO RELATED APPLICATIONS

This application represents the U.S. National Stage of International Application No. PCT/US2015/031697, filed May 20, 2015, which claims the benefit of U.S. Provisional Patent Application Ser. No. 62/000,692, filed May 20, 2014, and entitled "SYSTEM AND METHOD FOR FABRICATING ELECTROMAGNETIC FIELD ENHANCING OBJECTS FOR MAGNETIC RESONANCE IMAGING."

STATEMENT REGARDING FEDERALLY SPONSORED RESEARCH

This invention was made with government support under EB000215 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for designing and fabricating objects having desired electromagnetic properties to modify an electromagnetic field generated by an MRI system, such as to reduce inhomogeneities in a $B_0$ or $B_1$ field.

During an MRI scan, a strong magnetic field is formed around the area to be imaged. Ideally, the magnetic field is homogeneous, allowing for clear, undistorted images to be obtained. However, in many instances anatomical features or implants can cause localized magnetic field inhomogeneities that significantly affect the quality of the images that are obtained. For example, air-tissue boundaries in the nasal sinuses and ear canals can affect imaging of the brain, and air-tissue boundaries in the lungs can affect imaging of the spine and torso. In addition, artificial joints, such as those made of steel, can cause tremendous field inhomogeneities that can make magnetic resonance imaging around the joint nearly impossible. As a result, image quality, including signal-to-noise ratio and geometric distortion, is compromised by magnetic field non-uniformities that arise from the imaged subject.

Magnetic field inhomogeneities can be adjusted using "shimming" methods, which compensate for imbalances in the magnetic field. Localized adjustments in the field can be made by "active" shimming, using various configurations of shim coils that carry an adjustable electrical current. However, localized adjustments in the field can also be made by "passive" shimming, which involves positioning materials with differing magnetic properties and configurations within proximity of the anatomical region being imaged.

Diamagnetic and paramagnetic materials are, respectively, repelled by or attracted to an externally applied magnetic field, and can be used to construct passive shims for localized field adjustments. For example, an intra-oral "mouth shim" made of pyrolytic graphite (a diamagnetic material) has been shown to improve MRI of the frontal cortex. Cylindrical shims made of carved niobium (a paramagnetic material), arrayed in an adjustable shimming structure, have been used for MRI of the prefrontal and temporal regions of the brain. Similarly, combinations of blocks of bismuth (a diamagnetic material) attached to blocks of niobium (a paramagnetic material) mounted on an adjustable frame have been used for human brain imaging.

However, while shimming and other techniques are standard in MRI, these methods do not sufficiently improve image quality in many instances, and there is still a significant need for new methods to address the MRI problems that result from localized magnetic field inhomogeneities caused by patient anatomical features or implants.

SUMMARY OF THE INVENTION

The present invention overcomes the aforementioned drawbacks by providing a method for designing an object having desired electromagnetic properties that can be used to modify an electromagnetic field generated by a magnetic resonance imaging ("MRI") system. A magnetic field map for an MRI system is provided, and an object design is computed by optimizing a cost function that is based at least in part on an electromagnetic field generated by the MRI system as indicated in the provided magnetic field map. The object design defines a spatial distribution of at least one build material having known electromagnetic properties. The spatial distribution of the at least one build material having known electromagnetic properties will modify the electromagnetic field generated by the MRI system to achieve a desired change in the electromagnetic field.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for designing and fabricating three-dimensional objects with precisely computed material compositions for use in enhancing electromagnetic fields for magnetic resonance imaging ("MRI"). For instance, in some embodiments, the fabricated object can reduce magnetic field inhomogeneities in the main magnetic field of an MRI system. In some other embodiments, the fabricated object can reduce inhomogeneities in a transmit radio frequency ("RF") field (i.e., the $B_1$ field).

As mentioned above, one aspect of the present invention is a method for designing and fabricating a three-dimensional object that can be used to shim an electromagnetic field used in MRI, such as a $B_0$ or $B_1$ field. These objects can be placed around the area of a subject being imaged (e.g., the head for brain imaging) in order to reduce or eliminate local magnetic field inhomogeneities that can reduce image quality. As one example, the object could include a shim "mask" for the head to improve the quality of brain MRI. This mask could be similar to devices that are used for head and neck immobilization for radiotherapy, and in some instances could be used for MRI-guided radiotherapy planning applications.

The present invention includes a computational method for designing the object to be fabricated. For instance, the design method includes selecting the build materials and their spatial distribution in the fabricated object. The build materials would have known electromagnetic properties (e.g., known magnetic susceptibilities, known dielectric properties, or both), and the design method could compute the thickness, density, and distribution of the build materials in the object such that the desired effect on an electromagnetic field used during MRI can be achieved. For instance, the thickness, density, and distribution of the build materials in the object can be tailored to control the main magnetic field, $B_0$, within the area that will be imaged.

Multiple different build materials with differing electromagnetic properties could be used in a single fabrication, either simultaneously or sequentially, depending on what would be required to achieve the desired effect on the electromagnetic fields used during MRI. The electromagnetic properties of the materials could be diamagnetic, paramagnetic, ferromagnetic, dielectric, paraelectric, ferroelectric, or combinations thereof. Combinations of two or more build materials could also be used, thereby allowing for objects to be constructed that both "push" and "pull" the electromagnetic field outside of the imaged subject, as needed, to yield a more uniform electromagnetic field within the subject.

As an example, the build materials can include plastics with the desired magnetic susceptibilities or electrical properties. The computation of the object design, however, can also take into consideration other properties of the build materials, including mechanical properties, chemical properties, ease of use, cost, availability, and suitability for medical devices (e.g., biocompatibility). Examples of build materials include, but are not limited to, acrylonitrile butadiene styrene ("ABS"), high-density polyethylene ("HDPL"), polylactic acid ("PLA"), or any other suitable plastic, thermoplastic, or other material that can usefully be extruded to form a three-dimensional object.

In some instances, the build material can include a build material that is doped with another material in order to change the electromagnetic properties of the build material. For example, a build material can be doped with a diamagnetic compound, a paramagnetic compound, or a metal (e.g., a ferromagnetic metal). As an example, a build material can be doped with a ferromagnetic pigment, such as toner.

As an example, the fabricated object can include a passive shim that is placed adjacent a subject during an MRI scan. In some instances, the object can be custom fabricated for a specific subject. One example of a custom-fabricated object includes the shim mask mentioned above. Passive shims may otherwise include those used for improving the imaging of other parts of a subject's anatomy, such as the spine, the torso, the pelvis, and the extremities. The passive shims do not need to be subject-specific, however. Instead, the shims could be pre-manufactured shims that would be fabricated to cover a range of specific sizes, configurations, and materials.

The fabricated object may also include a passive shim that is designed as, or to be integrated into, the frame for a radio frequency ("RF") coil or for placement of the RF coil. In this example, the fabricated object helps obtain consistent coil locations from scan session to scan session for a given patient. The fabricated object may also include a housing for an RF coil, where the housing is designed to counteract field distortions caused by the presence of circuit components in the coil.

In some embodiments, the fabricated object may include a medical device or a part thereof. For instance, the fabricated object could include a surgical implant, such as an orthopedic implant, or a part of such an implant. As another example, the fabricated object could include part of an implanted cardiac device ("ICD"), such as a housing for the ICD. In the latter example, the design can be similar to the RF coil housing mentioned above, in which the housing is designed to counteract field distortions caused by the circuit components in the ICD.

Figure 1:
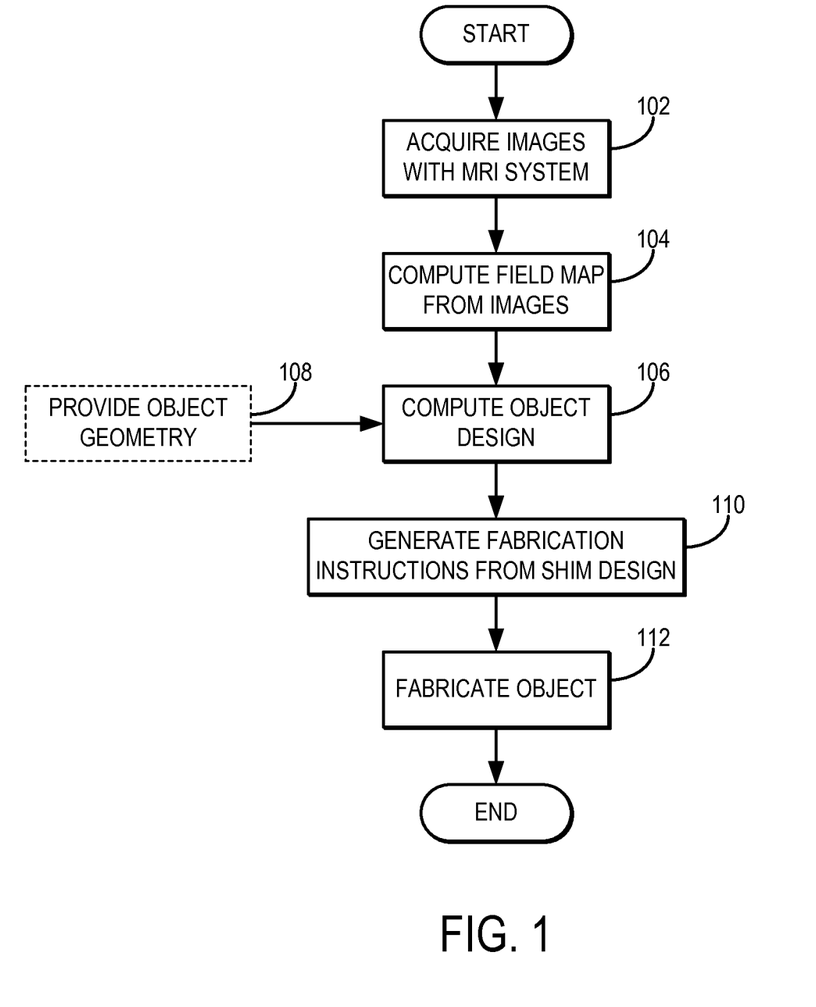
FIG. 1 is a flowchart setting forth the steps of an example method for designing and fabricating an object for modifying an electromagnetic field of an MRI system.

Referring now to FIG. 1, a flowchart is illustrated as setting forth the steps of an example of a method for designing and fabricating an object with magnetic properties, electrical properties, or both, that are specifically tailored to achieve a desired effect on electromagnetic fields, such as $B_0$ and $B_1$ fields, generated by an MRI system. The method includes acquiring images with an MRI system, or otherwise providing images previously acquired with the MRI system, as indicated at step 102. As one non-limiting example, the images can be acquired using a dual gradient-recalled echo or dual tip angle ("GRE") pulse sequence.

Depending on the application, these images can be acquired with a particular subject in the MRI system, or can be acquired with no subject in the MRI system. For instance, of the object to be manufactured is subject-specific, then it is preferable that the images be acquired while that subject is in the MRI system. An example of subject-specific objects include subject-specific passive shims, an immobilization mask for radiation treatment applications, and surgical implants or parts thereof.

From the acquired images, a field map is computed, as indicated at step 104. In some embodiments, the field map is a $B_0$ field map. In some other embodiments, the field map may be a $B_1$ field map.

An object design is then computed based on the field map, as indicated at step 106. The object design defines how to fabricate an object to achieve the desired effects on one or more electromagnetic fields generated by the MRI system. For instance, the object design may be computed such that the fabricated object minimizes variations in the $B_0$ field. In some embodiments, however, the object design may be computed such that the fabricated object obtains a desired effect on a generated $B_1$ field, such as reducing variations in the $B_1$ field. In the latter example, the object design may be computed based not only on the magnetic properties of the build materials, but on their electric properties.

In general, the object design can be computed using a suitable algorithm for optimizing a suitable cost function based at least in part on obtaining a desired spatial distribution of electromagnetic properties that achieves the desired modification of an electromagnetic field generated by the MRI system. For instance, a region growing method based on a source point or source surface can be used. In some embodiments, an unconstrained optimization can be used. As an example, an unconstrained optimization with retrospective region bridging can be used.

In region growing algorithms, the optimization process is iterative. Starting at a given fixation point or surface, each iteration will distribute upon the object surface the placement of build materials or air. This object design will build up a fabricated object volume one concentric layer per iteration. Iteration can continue until a specified stopping criterion is satisfied. For example, iteration can continue until there is less than one percent change in the value of the optimization cost function, or until the object volume exceeds the maximum allowable object volume, constrained by the surface of the subject, imaging coil, fabrication system build volume, or combinations thereof.

It is noted, however, that objects that are larger than the available build volume of the fabrication system can be designed and fabricated. In these instanced, the object will be divided into subcomponents that can fabricated within the fabrication system. These subcomponents can be designed to have edge features that allow the interlocking of the subcomponents into the full object without the need for an additional adhesive. This "snap together" construction can ensure a precise alignment of the subcomponents while avoiding the confounds associated with additional adhesives.

In an unconstrained optimization algorithm with retrospective region bridging, the distribution of two build materials and air that minimizes the optimization cost function can be computed over a volume that is only constrained by the subject, coil, and build volume. After the optimal distribution is computed, disjoint regions can be connected with posts of minimal length, printed with the material that has the closest magnetic susceptibility to air.

It is noted that the unconstrained optimization may yield structures that are challenging to fabricate due to the presence of overhangs. If there are sizable overhangs, support structures may need to be fabricated. It is possible, however, to design the object such that the support structures can be removed after the object has been fully fabricated and, thus, more fully structurally supported. As an example, in these instances, a dissolvable build material can be used for the support structures and the optimization algorithm can be limited to designing the object with a different build material that is not dissolvable with the same solvent as the dissolvable build material. In this instance, the support structures can then be designed as necessary using the dissolvable build material and, after fabrication, the support structures can then be removed by dissolving with dissolvable build material with the appropriate solvent, which may include water.

In some embodiments, the optimized cost function can be based on the variation in polarizing field, $B_0$, magnitude within a region-of-interest. This cost function is applicable for magnetic resonance spectroscopy experiments and for acquisitions in which geometric fidelity is of high importance. In some other embodiments, the optimized cost function can be based on the amplitude of the polarizing field, $B_0$, gradient within a region-of-interest. This cost function is suited for minimizing intra-voxel dephasing, resulting in $T_2$-signal decay and, thus, signal voids.

In some embodiments, the object design can be computed for the entire volume of the object at once. In other embodiments, the object design can be computed for a surface and then iterated to create a layering of such surfaces. In still other embodiments, the object design can be computed in a voxelwise fashion, whereby the object design is voxelized and the deposition of build materials is based on building up unit volumes, such as voxels, of the object. As an example, the fabrication resolution of a voxelwise build is determined by the fabrication system, which in some instances can be as fine as 0.1 mm. Coarser build resolutions than those attainable with the fabrication system can also be used, however.

As an example, the object design may include computing 5 mm isotropic build voxels of uniform build material. By using a coarser build resolution, the dimensionality of the optimization process can be significantly reduced, thereby reducing the computational burden of the design algorithm.

The limitation of printing with only two materials, plus voids, can significantly confine the optimization capabilities of the system. Thus, as another example, the object design may include designing each build voxel to contain a mixture of the two build materials. In this example, each build voxel can have a magnetic susceptibility along a continuum between the susceptibilities of the two selected build material. For instance, each build voxel can be fabricated using any suitable pattern of alternating build materials, including layered patterns, such as layered checkerboard patterns. As one specific example, each layer of the build voxel may include altering regions of 0.4 mm isotropic in-layer width and 0.1 mm layer thickness. In these examples, the percentage of regions of each build material will weight the magnetic susceptibility towards the magnetic susceptibilities of the individual build materials. This method better reduces the optimization dimensionality if compared to simply increasing spatial resolution.

In some instances, the voxelwise object design can be binary, in which each voxel is assigned to be filled by one of two different available build materials, as noted above. In these instances, the object design will contain only two different build materials, preferably one with a highly diamagnetic susceptibility value and one with a highly paramagnetic susceptibility value. In other voxelwise designs, however, more than two different build materials can be used to provide intermediate values of magnetic susceptibilities.

The object design can be computed with any number of different constraints on the size and shape of the fabricated object. For instance, the shape and size of the object can be constrained to the available space in the bore of the MRI system, or can be constrained to be placed adjacent another object in the bore of the MRI system. As an example, the shape and size of the object can be constrained to be placed adjacent a particular RF coil, immobilization mask, or subject.

In some embodiments, the shape and size of the object may be predetermined, and the object design is thus computed to be constrained to the predetermined shape and size of the object. As an example, the object design may be computed for a surgical implant, a medical device, or parts thereof. In this instance, the object design can be computed to best minimize the field variations generated in the presence of the surgical implant or other medical device. In these applications, the geometry of the particular object can be provided, as optionally indicated at step 108.

Referring again to FIG. 1, when the object design has been computed, fabrication instructions are generated based on the computed object design, as indicated at step 110. As one example, an STL file can be generated from the object design, and g-code can be generated from the STL file. As another example, the fabrication instructions can include instructions based in any other suitable numerical control programming language.

The fabrication instructions are then communicated to a fabrication system to fabricate the object with the desired magnetic properties, electrical properties, or both, as indicated at step 112. The fabrication system may include a 3D printer system, but may also include those fabrication systems that utilize compression molding, thermoforming, lamination, or combinations of different fabrication methods. Where the fabrication system is a 3D printer system, the 3D printer may use fused deposition modeling, or similar techniques, where a bead of material is extruded in a series of two dimensional paths to form a three-dimensional object. As another example, the 3D printer may use other additive fabrication techniques, including multijet printing, stereolithography, digital light processor ("DLP") three-dimensional printing, selective laser sintering, and so on.

Figure 2:
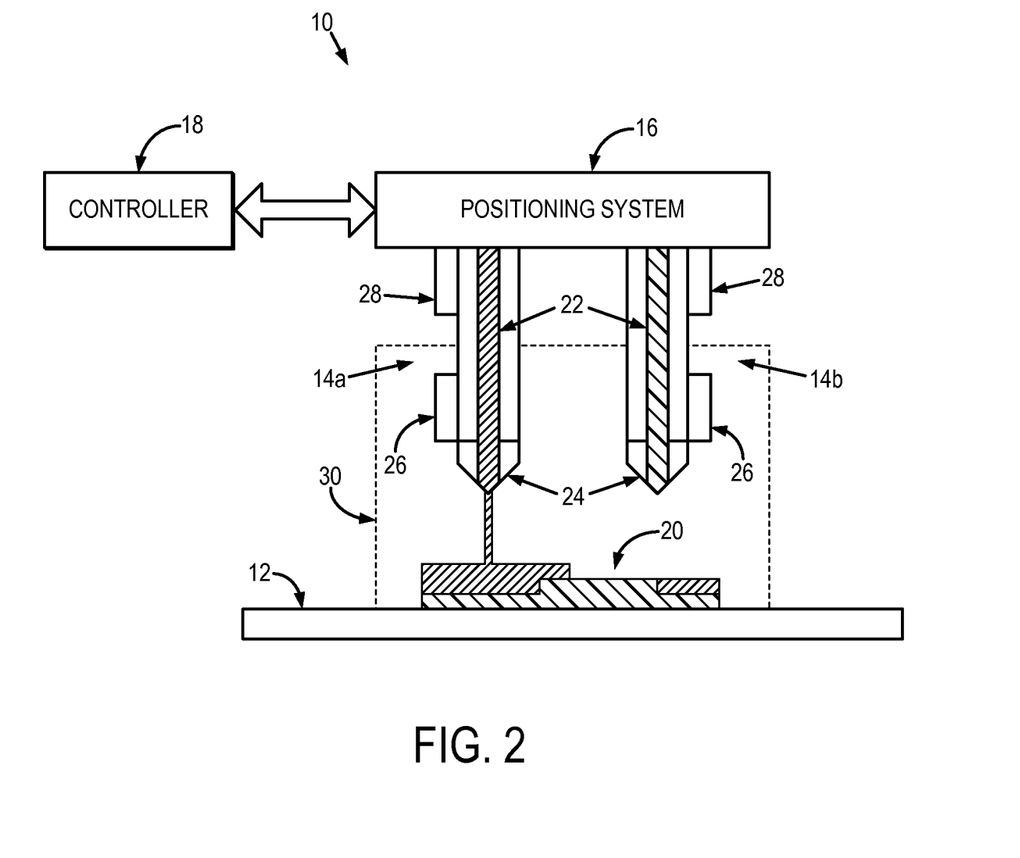
FIG. 2 is a block diagram of an example three-dimensional printing system that can be used to fabricate an object designed according to the method of FIG. 1.

Referring now to FIG. 2, a block diagram of an example three-dimensional ("3D") printer that can be used when implementing the present invention is illustrated. In general, the printer 10 may include a build platform 12, a first extruder 14a, a second extruder 14b, a positioning system 16, and a controller 18. The positioning system 16 allows the extruders 14a, 14b to move relative to the build platform 12 in order to fabricate an object 20 while one or both of the extruders 14a, 14b deposit build material. The build platform 12 is preferably has a rigid and planar surface on which the object 20 is fabricated in a build volume 30.

Each extruder 14a, 14b may include a chamber 22 in an interior thereof to receive a build material. As described above, the choice of material is guided by the design algorithm and multiple different build materials may be used when fabricating a particular object.

Each extruder 14a, 14b may include an extrusion tip 24 that extrudes build material in a desired cross-sectional shape. Each extruder 14a, 14b may include a heating element 26 to melt thermoplastic or other meltable build materials within the chamber 22 for extrusion through the extrusion tip 24 in liquid form. The extruder 14a, 14b may also include a motor 28 to push the build material into the chamber 22, through the extrusion tip 24, or both.

As one example of operation, a build material such as an ABS plastic in filament form may be fed into the chamber 22 from a spool or the like by the motor 28, melted by the heating element 26, and extruded from the extrusion tip 24. By controlling a rate of the motor 28, the temperature of the heating element 26, other process parameters, or combinations thereof, the build material may be extruded at a controlled volumetric rate.

The positioning system 16 may generally be adapted to three-dimensionally position the extruders 14a, 14b and the extrusion tips 24 such that the extruders 14a, 14b deposit build material in accordance with a previously computed object design. In general, the object may be fabricated by depositing successive layers of material in two-dimensional patterns determined by the computed object design.

The printer 10 is operated under control of a controller 18 that is in communication, such as wired or wireless communication, with the positioning system 16, the build platform 12, and other components of the printer 10. In general, the controller 18 is operable to control the components of the printer 10, such as the build platform 12, extruders 14, and positioning system 16 to fabricate the object 20 from the suitable build materials. The controller 18 may include any combination of software, processing circuitry, or both suitable for controlling the various components of the printer 10. As an example, the controller may include a microprocessor, microcontroller, application-specific integrated circuit ("ASIC"), programmable gate arrays, and any other digital or analog components. In some embodiments, the controller 18 may be a processor associated with a personal computer or other computing device that is in communication with the printer 10. Thus, in some embodiments the controller 18 can be configured or otherwise programmed to perform the object design algorithms described above.

Figure 3:
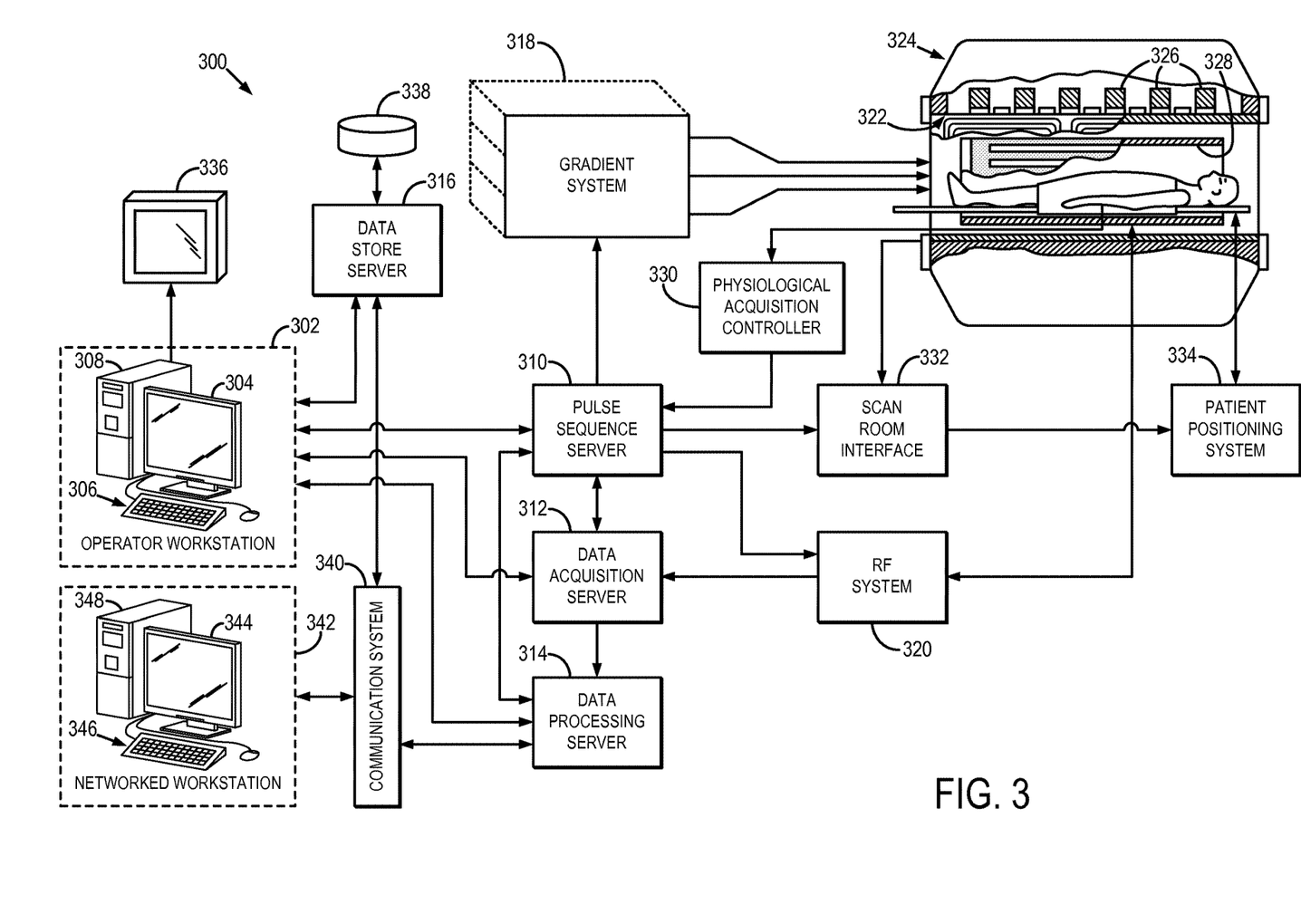
FIG. 3 is a block diagram of an example of an MRI system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \tag{1};$$

and the phase of the received magnetic resonance signal may also be determined according to the following relationship:

$$\varphi = \tan^{-1}\left(\frac{Q}{I}\right). \tag{2}$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for designing an object having desired electromagnetic properties to modify an electromagnetic field generated by a magnetic resonance imaging (MRI) system, the steps of the method comprising:
   (a) providing to a processor, a magnetic field map for an MRI system;
   (b) computing with the processor, an object design by optimizing a cost function that is based at least in part on an electromagnetic field generated by the MRI system as indicated in the provided magnetic field map, the object design defining a spatial distribution of unit volumes each containing a deposition of at least one build material having known electromagnetic properties;
   (c) generating with the processor, instructions for a fabrication system to fabricate an object based on the computed object design;
   (d) communicating the instructions to the fabrication system in order to control the fabrication system to fabricate the object according to the computed object design; and
   wherein the spatial distribution of the at least one build material having known electromagnetic properties will modify the electromagnetic field generated by the MRI system to achieve a desired change in the electromagnetic field.

2. The method as recited in claim 1, wherein the cost function is based at least in part on a variation in a polarizing magnetic field of the MRI system.

3. The method as recited in claim 1, wherein the cost function is based at least in part on an amplitude of a gradient of a polarizing magnetic field of the MRI system.

4. The method as recited in claim 1, wherein the fabrication system is a three-dimensional printing system.

5. The method as recited in claim 1, wherein the at least one build material is selected from the group consisting of acrylonitrile butadiene styrene (ABS), high-density polyethylene (HDPL), polylactic acid (PLA), and combinations thereof.

6. The method as recited in claim 1, wherein the at least one build material is mixed with another material to achieve the known electromagnetic properties.

7. The method as recited in claim 6, wherein the another material includes a ferromagnetic metal.

8. The method as recited in claim 1, wherein the known electromagnetic properties comprise magnetic susceptibility values.

9. The method as recited in claim 8, wherein the generated electromagnetic field is a polarizing magnetic field.

10. The method as recited in claim 9, wherein the provided magnetic field map is a $B_0$ map.

11. The method as recited in claim 1, wherein the known electromagnetic properties comprise dielectric values.

12. The method as recited in claim 11, wherein the generated electromagnetic field is a transmit radio frequency (RF) field.

13. The method as recited in claim 12, wherein the provided magnetic field map is a $B_1$ map.

14. The method as recited in claim 1, wherein the object design is computed by the processor based on an entire volume of the spatial distribution.

15. The method as recited in claim 1, wherein the object design is computed by the processor based on a successive layering of build material.

16. The method as recited in claim 1, wherein the object design is based on a plurality of build voxels that collectively define the spatial distribution.

17. The method as recited in claim 16, wherein each of the plurality of build voxels is composed of a uniform build material.

18. The method as recited in claim 16, wherein at least one of the plurality of build voxels is composed of a mixture of at least two different build materials, each having different known electromagnetic properties.

\* \* \* \* \*